United States Patent
Dotson et al.

(10) Patent No.: US 11,237,149 B2
(45) Date of Patent: Feb. 1, 2022

(54) COMPONENT MEASUREMENT OF A FLUID

(71) Applicant: HALLIBURTON ENERGY SERVICES, INC., Houston, TX (US)

(72) Inventors: Adam Robert Dotson, Houston, TX (US); Brice Aaron Jackson, Houston, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 41 days.

(21) Appl. No.: 16/743,170

(22) Filed: Jan. 15, 2020

(65) Prior Publication Data
US 2021/0215659 A1 Jul. 15, 2021

(51) Int. Cl.
*G01N 33/28* (2006.01)
(52) U.S. Cl.
CPC .................................. *G01N 33/2823* (2013.01)
(58) Field of Classification Search
CPC .................................................. G01N 33/2823
USPC ....................................................... 73/64.56
See application file for complete search history.

(56) References Cited

U.S. PATENT DOCUMENTS

| 1,972,929 A * | 9/1934 | Fisher ........................ C10B 1/10 202/118 |
| 4,374,704 A * | 2/1983 | Young ........................ C10B 1/10 15/93.2 |
| 5,174,149 A | 12/1992 | Grob et al. |
| 7,615,189 B2 | 11/2009 | Aslam et al. |
| 7,625,532 B2 * | 12/2009 | Bridgwater ............... C10B 7/02 422/198 |
| 8,123,046 B2 * | 2/2012 | Billeaud ............... B01D 29/014 210/409 |
| 8,569,685 B2 | 10/2013 | Finlay |
| 2013/0277113 A1 | 10/2013 | Murphy |
| 2015/0354352 A1 | 12/2015 | Ezzat et al. |
| 2017/0138191 A1 | 5/2017 | Patil et al. |
| 2019/0064039 A1 | 2/2019 | Ammar et al. |

OTHER PUBLICATIONS

International Search Report and Written Opinion for International application No. PCT/US2020/014600, dated Oct. 12, 2020, 11 pages.

* cited by examiner

*Primary Examiner* — Nimeshkumar D Patel
*Assistant Examiner* — Jean F Morello
(74) *Attorney, Agent, or Firm* — Polsinelli PC

(57) ABSTRACT

An apparatus for measuring the oil and water fractions of a fluid, such as a drilling fluid. The apparatus includes a vessel body having an inner chamber coupled with a fluid inlet and an outlet. A heating element is coupled with the vessel body operable to communicate heat sufficient to vaporize a fluid within the vessel body to a gas. A gas analytical device is coupled with the outlet operable to measure components of the gas exiting the vessel body via the outlet. A rotary milling cutter translatable through the inner chamber and into solids remaining from the vaporized fluid, and having cutters operable to break solids within the inner chamber remaining from the vaporized fluid. The solids may be ejected through a solids discharge port.

20 Claims, 6 Drawing Sheets

COMPONENT MEASUREMENT OF A FLUID

FIELD

The present disclosure pertains to determining components of fluids, and in particular, the present disclosure relates to analysis of fluids for determining the amount and relative fractions of components in a fluid.

BACKGROUND

Drilling operations are conducted to reach subterranean formations containing hydrocarbon reservoirs. Drilling often involves the use of fluids referred to as a drilling fluid or drilling mud. The drilling fluid is pumped from the surface through the drill string, out of the drill bit and circulated back to the surface. The drilling fluid acts as a lubricant and also removes cuttings formed by the drilling process. The drilling fluid may be made up of various components, which may include for instance water, hydrocarbons (oil), and solids.

The composition of the drilling fluid is monitored to assure it meets desired specification, including the relative amounts of the components. In order to make this determination, often a retort is used. A retort is a vessel in which a fluid is added and heated to beyond its boiling point to a gas. The retort often has a long neck in which the vapor condenses to a liquid which is then measured with a graduated cylinder to determine the relative amounts of oil and water. Solids are left behind within the vessel as the initial fluid is vaporized. In order for re-use the retort must be cleaned, and due to the high heat the solids form strong blocks within the vessel and films along the vessel surface which may be difficult to remove. Accordingly, many manual steps are required for monitoring the composition of the drilling fluid using the retort.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings in which.

DETAILED DESCRIPTION

Figure 1:
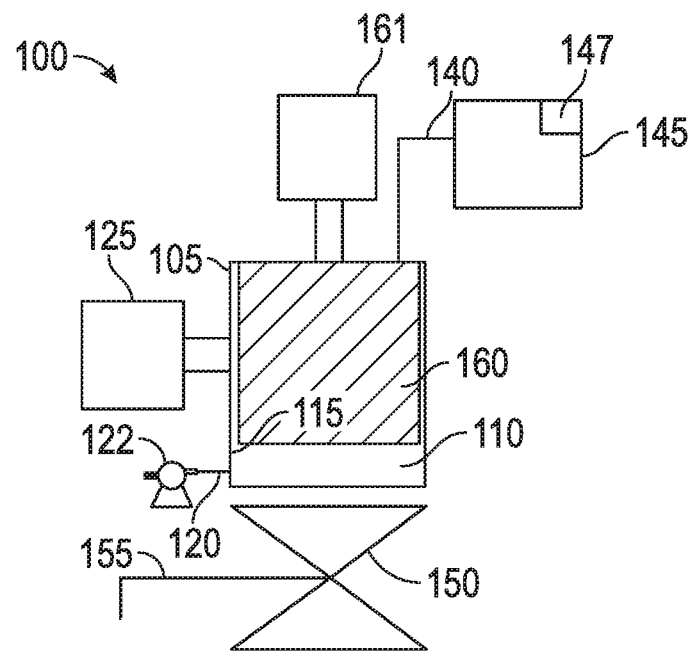
FIG. 1 is a schematic diagram of an exemplary fluid composition measurement apparatus, in accordance with the present disclosure.

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure. Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by the practice of the principles set forth herein.

Disclosed herein is an apparatus, method and system for determining the amounts and relative fraction of components of a fluid, including oil and water fractions, as well as solids. The fluid may be a drilling fluid, fracturing fluid, production fluid, and may be in liquid form. The fluid is introduced into an inner chamber of a vessel body. The vessel body and/or inner chamber is heated to vaporize the fluid into a gas phase. Upon vaporization any solids originally in the fluid are separated out and remain in the vessel body as the gas exits the inner chamber. The gas is then provided to a gas analytical device to determine the components and relative amounts of the composition, wherein the analytical device may include a chromatograph, spectrometer, and/or spectroscopy, including a chromatograph, spectrometer, and/or spectroscopy, including include infrared absorption (IR), gas chromatography (GC), mass spectrometry (MS), gas chromatography and pass spectrometry (GC-MS), IR spectroscopy, UV-Fluorescence spectroscopy, and UV-VIS spectroscopy.

The gas analytical device may detect the compounds in the gas and can characterize the types and amounts of compounds. The quantity of fluid entering the vessel body can be a known and/or predetermined quantity. Accordingly, with the information regarding the amount and type of compounds detected by the gas analytical device, along with the amount of fluid introduced into the vessel, the difference provides the volume of solids that were in the fluid. Accordingly, each of the liquid and solid components can be determined and the relative amounts and types of the liquid compounds of the fluid can be determined.

The process and determination can be made on a continuous or batch basis. In a continuous process, the known quantity input of fluid may be a flow rate, and in a batch process can be conducted each time with a known and/or predetermined amount.

After a predetermined period of time or quantity of fluid, or number of batches, the solids within the inner chamber may be removed. The solids build-up may form high strength layers or bodies. For instance the solids may form a hard film on the surface or walls of the inner surface of the inner chamber or form volume of solids. The surface of the inner chamber may be cylindrical and so may form a hard puck or other shape according to the corresponding shape of the inner surface. To remove the solids they may be broken up by milling or use of cutters. In particular, a rotary milling cutter may be employed which simply rotates or translates a distance within the inner chamber to grind, cut or otherwise break up the solids within the inner chamber. The cutters or blades of the rotary milling cutter may scrape against the surface of the inner chamber to remove the solids. The solids may be ejected from a solids discharge port through which the broken.

The operation of the apparatus can be fully or partially automated to reduce manual action. For instance, the fluid, vaporization of the fluid, the detection by the gas analytical device and the milling removal of the solids can be carried out in a continuous automated fashion. For continuous operation fluid or drilling fluid from a drilling operations can be provided to the apparatus in a predetermined flow rate with the components and fractions measured by the gas analytical device, and the milling and cleaning carried out periodically at predetermined times. The same can be carried out except modified for batch processes where batches of fluid in predetermined and/or known quantities provided to the apparatus for measurement.

FIG. 1 illustrates a fluid composition measurement apparatus 100 having a main vessel body 105. The main vessel body 105 has an inner chamber 110. The inner chamber 110 can be sized to have a sufficient volume for retaining liquid and/or vapor for testing. The inner chamber 110 has a surface 115 which may be a smooth texture. Fluid may be introduced into the inner chamber 110 via an inlet 120 and vaporized to a gas phase. A pump 122 may be provided for injecting the fluid into the inlet 120. The pump 122 may be for instance a peristaltic or micro-metering pump. A heating element 125 may be coupled with the vessel body 105 to provide heat sufficient to vaporize the fluid entering inner chamber 110. The heating element 125 may be a separate heater or may be integral with the body of the main vessel body 105. The heating element may be an electric, oil or gas powered heater and radiate heat into the inner chamber 110. The fluid entering the inner chamber 110 is in a liquid phase but may be immediately vaporized, or it may enter the inner chamber 110 and be vaporized over time as it is exposed to heat. The fluid entering the inner chamber 110 may be a mixture of oil, water and solids, and so the temperature may be sufficient to vaporize all liquid components of the fluid. The temperature may range from 90° C. to 200° C., alternatively from 100° C. to 150° C.

Upon vaporization of the fluid, the gas may exit the outlet 140 at or proximate the top of the inner chamber 110. The gas may then enter a gas analytical device 145. The gas analytical device 145 detects the type and amounts, concentration, and/or fraction of compounds in the gas. A control unit 147 may be communicatively coupled with and integrated with the gas analytical device 145. The control unit 147 can control the operation of the gas analytical device 145 as well as analyze the results and determine the compounds and relative amounts or concentration of compounds within the gas.

As the fluid is vaporized the solids contained in the fluid remain in the inner chamber 110. Due to the high temperatures the solids may form a high strength film along the surface 115 of the inner chamber 110, and may also form a strong block at the base of the inner chamber 115. In order to remove the solids they must first be broken or ground to sufficiently small particles or pieces and discharged through the solids discharge valve 150 and it's the valve outlet 155. A rotary milling cutter 160 is provided having cutters, such as blades, teeth or splines, which grind and otherwise break the solids apart for expelling the solids via discharge valve 150. The rotary milling cutter 160 may be translated vertically from top to bottom, or from bottom to top inner chamber 110 to cut into the solids. Further, the cutters of the rotary milling cutter 160 may extend to and contact the surface 115 of the inner chamber 110 to scrape solids from the surface 115 upon rotation.

A motor 161 may drive the rotation or translation of the rotary milling cutter 160. The motor 161 may be one or more electrical motors, such as a brushless DC electrical motor, including stepper motors or may be a gas powered motor. The inner chamber 110 may be flushed with an inert gas or liquid to assist in expelling any remaining solids. After a predetermined period of time, or alternatively, predetermined number of batches, or alternatively, predetermined amount of fluid or gas provided to the apparatus 100, or alternatively, after the buildup up a predetermined mass or volume of solids, the solids may be broken up and discharged. The point at which the buildup of the solids is such that removal is required may be determined experimentally or based on material balances.

Figure 2A:
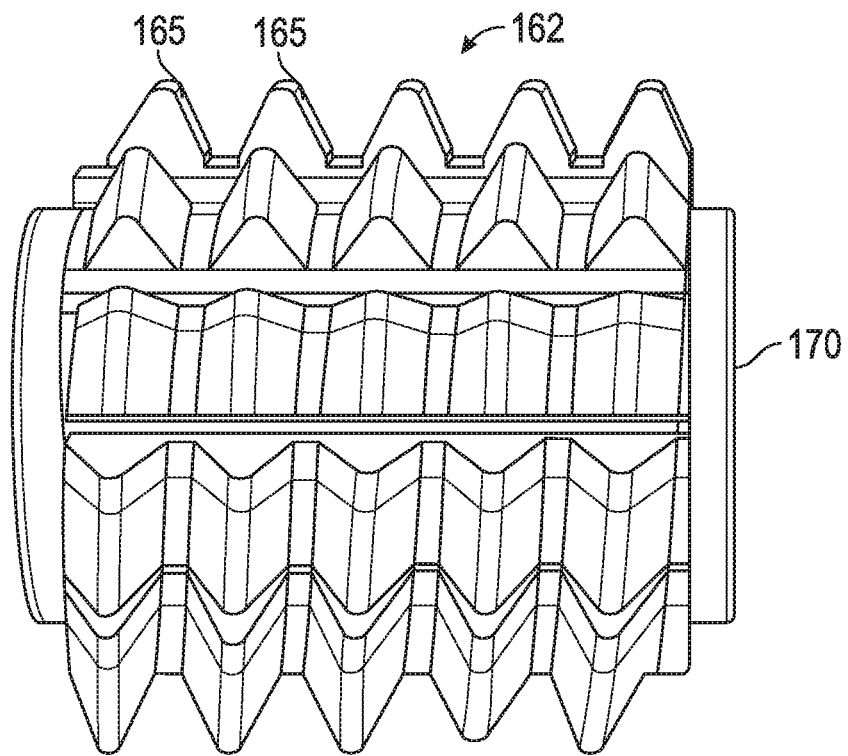
FIG. 2A illustrates a side view of an embodiment of a milling hob, in accordance with the present disclosure.
Figure 2B:
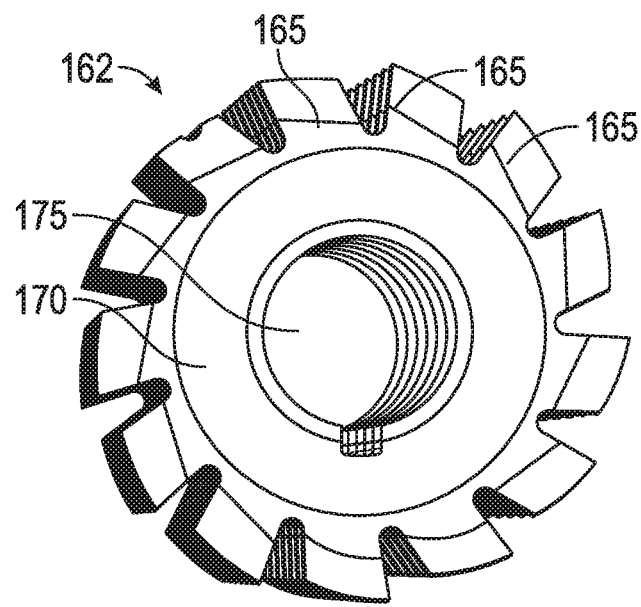
FIG. 2B illustrates a front view of an embodiment of a milling hob, in accordance with the present disclosure.
Figure 2C:
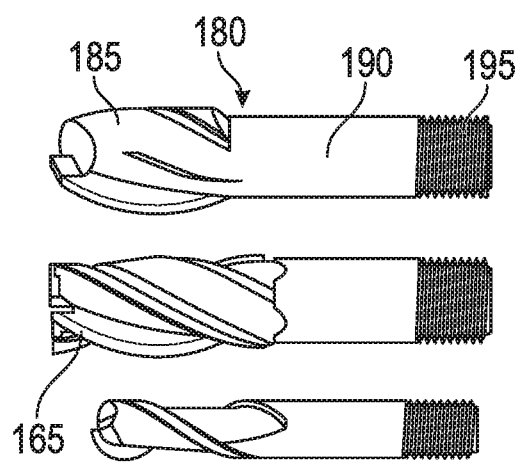
FIG. 2C illustrates a front view of an embodiment of an end mill, in accordance with the present disclosure.

FIG. 2A illustrates a side view of a milling hob 162 which may be a hob portion of the rotary milling cutter 162. As shown, a plurality of cutters 165 project from the central body 170. FIG. 2B illustrates a front view of the rotary milling hob 162 having a central canal 175 and a plurality of cutters 165 projecting from the central body 170. FIG. 2C illustrates an end mill 180 having a main body 190 with front cutter 185. The end mill 180 has a threaded portion 195 which can be threaded into the milling hob 162 to form the rotary milling cutter 160. The milling hob 162 and the end mill 180

The gas analytical device 145 of FIG. 1 may be any device capable of determining the type and/or amounts, fraction, and/or concentration of the vaporized gas. Exemplary analytical gas devices may include a chromatograph, spectrometer, and/or spectroscopy, including include infrared absorption (IR), gas chromatography (GC), mass spectrometry (MS), or gas chromatography and mass spectrometry (GC-MS), IR spectroscopy, UV-Fluorescence spectroscopy, and UV-VIS spectroscopy.

Figure 3:
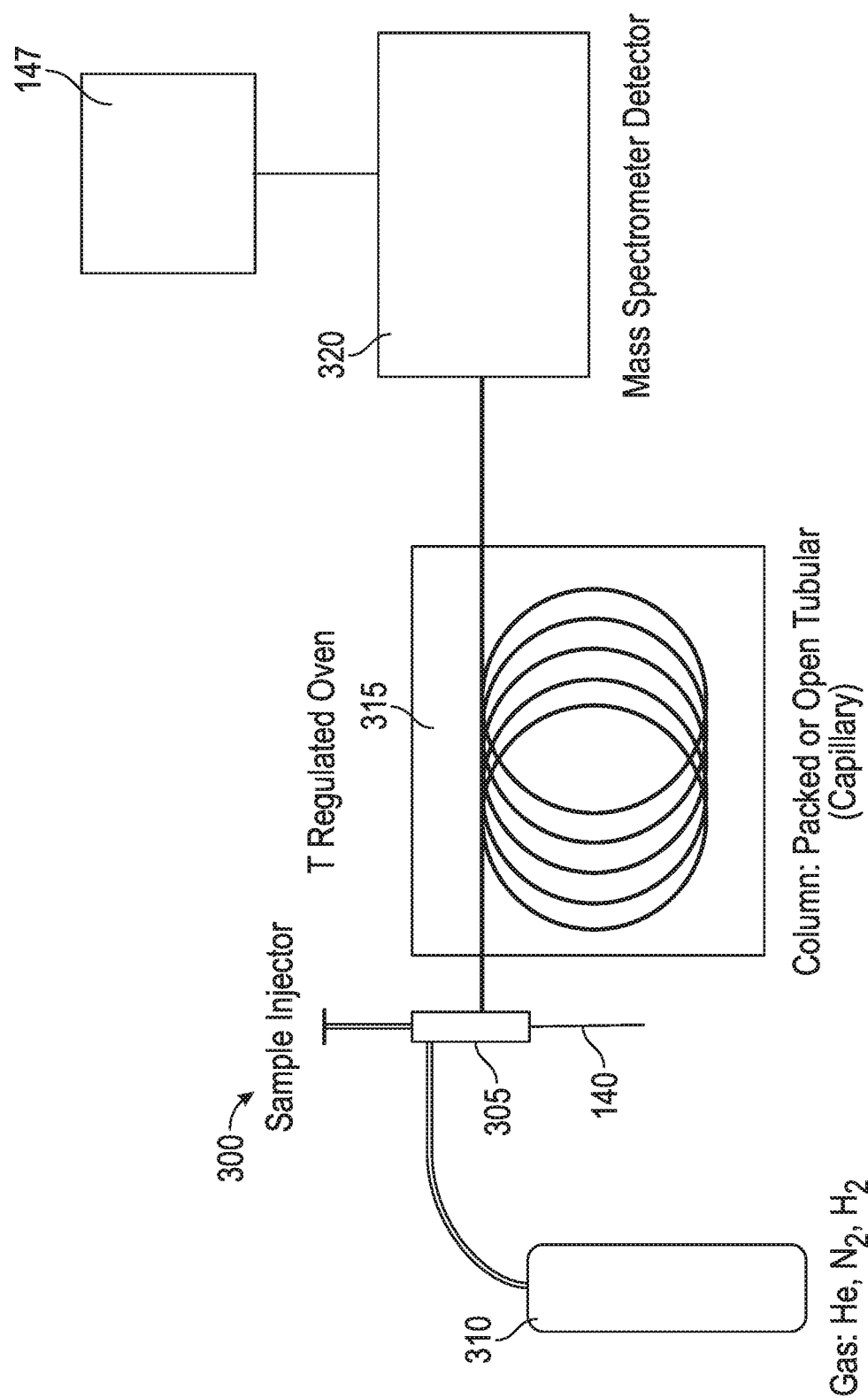
FIG. 3 illustrates an example GC-MS instrument as an exemplary gas analytical device, in accordance with the present disclosure.

FIG. 3 illustrates an exemplary GC-MS 300 as an exemplary gas analytical device. As shown a vaporized gas is provided to an injector 305 of the GC-MS 300 via outlet 140 from the fluid composition measurement apparatus 100 illustrated in FIG. 1. A carrier gas 310 may be provided with the vaporized gas, which together are injected into the GC column 315. The carrier gas may be any inert gas (does not react with the gas components) such as helium, nitrogen, hydrogen, or air. The retention times within the GC may depend on the components in the gas. The various components separate as they pass through the GC column and which elutes the components into an ionization source and MS detector 320. Electrical or chemical ionization, or other ionization method may be employed. The ionized components detected by the MS detector 320 and may be filtered by their mass to charge ratios and identified by their mass spectra and molecular ion peaks. The MS detector 320 may employ one or a plurality of the following: quadrupole, ion trap, linear ion trap, time of flight (TOF), triple quadrupole, monopole, Fourier transform (FT), magnetic sector, crossfield, rotating field, orbital ion trap, linear ion trap, rectilinear ion trap or cyloidic.

The control unit 147 may be used to control the operation of the GC-MS 300 and may also process and display the results. Accordingly, the results may be displayed for an operator to evaluate and/or modify. The results from both the GC and the MS portions of the GC-MS 300, for instance a chromatogram may be processed and/or displayed along with peaks for corresponding compounds and according to their retention times. The results from the spectrogram processed and/or displayed by the control unit 147 including spectrums or spectrograms which are used to identify the particular components. The data from each of the GC and MS may be used for determining the fractions and types of components. The GC 315 separates the components, but additionally, the peaks in the chromatogram may assist determination of the component type. Furthermore, the areas under the peaks may be calculated for one or more of the components to determine the relative fraction of each of the components. The areas can be calculated manually or automatically by the control unit 147. Further, as mentioned, the spectrograms from the MS 300 also provide confidence as to the identity of the components. When the process is continuous, the GC-MS or other gas analytical device may be time-averaged and used to indicated continuous trends of oil and water content.

The amounts, fraction, and/or concentration of each of the components as well as solids may be determined based on the amounts provided to the inlet of the measurement apparatus. In a batch process, a predetermined or otherwise known quantity of fluid may be provided into the inner chamber for vaporization. This may be a known volume, or mass. In a continuous process, the predetermined amount metered at a particular flow rate, such as volume/time rate. Based on this input, the fluid may be vaporized to a gas, and the amounts and type of components in the gas determined by the gas analytical device. Upon subtracting the total amounts of the gas components from the fluid (liquid) input, the amount, in volume or mass, of solids separated from the fluid upon vaporization and remaining in the inner chamber may also be determined.

The flow rate in a continuous process may be from about 0.5 ml/min to 20 ml/min, alternatively from about 1 to 10 ml/min, alternatively from 4 to 7 ml/min and combinations of the aforementioned ranges.

The components which may be determined may include oil and water. Many drilling fluids are made up of oil and water mixtures, both water based drilling fluids as well as oil based drilling fluids, often referred to as invert emulsions. Each of the oil and water fractions may be determined, as well as the components making up the oil fraction to the extent more than one type of oil is employed. Additionally, other vaporized components may be determined such surfactants or other additives.

The drilling fluid may have as its base water, or one or more natural oil or synthetic oils and fluids, such as, for example, the esters, olefins, paraffins, and ester blends. The drilling fluid may be a water based emulsion where water is the predominant and continuous phase, and there is an oil phase dispersed in the water, therefor having a discontinuous oleaginous phase. The drilling fluid may be an invert emulsion, having a continuous oleaginous phase and a discontinuous water phase. The water may be in the form of saltwater, brine, seawater, freshwater, and may be any aqueous based solution. In instances, the invert emulsions drilling fluids according to this disclosure have an oil to water ratio ranging from above 50:50 to about 98:2, including all subranges therein between. Various suitable ranges of oil to water may include for instance, 74:26 and about 80:20, including all sub-ranges therein between about 75:25 or greater, about 80:20 or greater, about 85:15 or greater, or between about 90:10 and 60:40. Various additives may be provided including gelling agents, emulsifiers, weighting agents, organic clays, viscosifiers, emulsifiers, rheology agents, surfactants and shale encapsulators. Sufficient amount of gelling agents and other additives may be added to the base fluid to cause gelation and thixotropic properties and achieve predetermined gel strength at rest. In some instances, the drilling fluid has a density in the range of from about 9 ppg (1080 kg/m$^3$) to about 18 ppg (2160 kg/m$^3$).

Figure 4A:
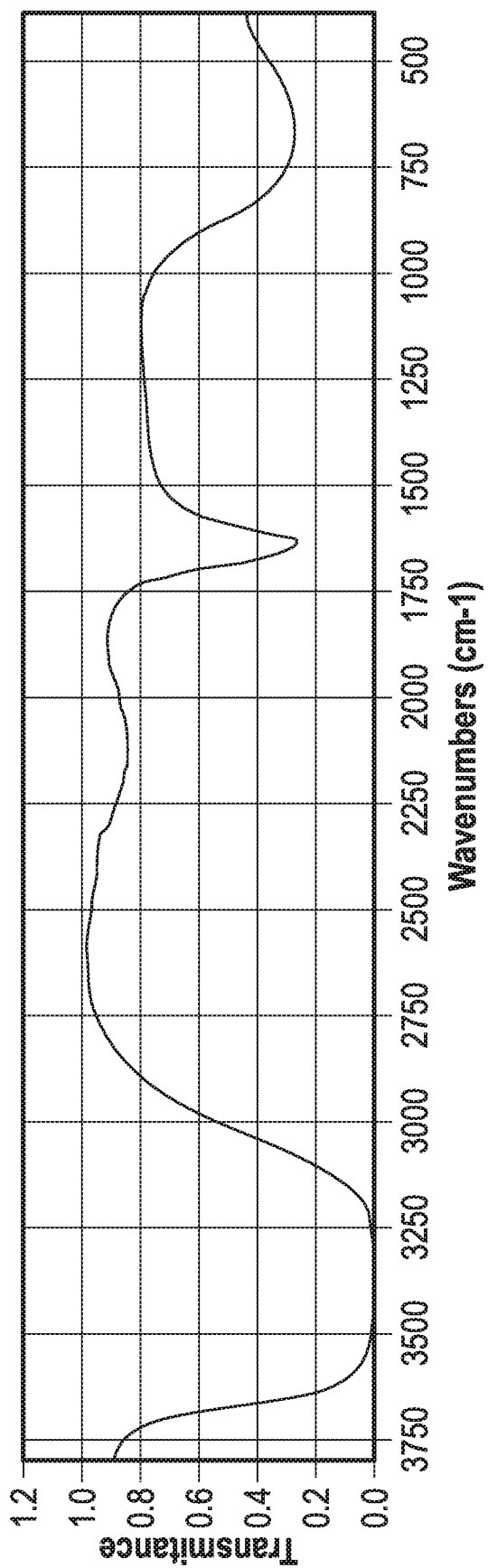
FIG. 4A illustrates the spectrum for water.
Figure 4B:
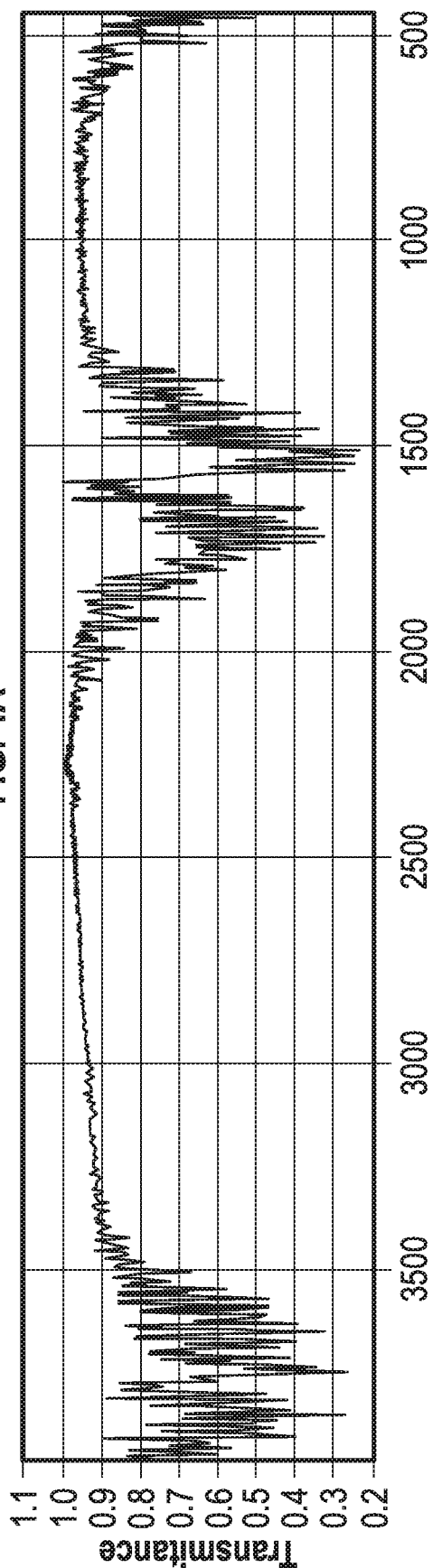
FIG. 4B illustrates the spectrum for steam.

As disclosed herein the analytical gas instrument may be calibrated to increase accuracy. FIGS. 4A and 4B illustrate the spectrum for water and steam, respectively. If water is condensed while entering the outlet of the inner chamber or the entering the gas analytical device, its mass fraction can be included in the total reported H$_2$O fraction. This may assist in preventing under-reporting of the volume of water in a sample, which otherwise would cause error in the oil to water ratio reported.

The process may be fully automated and may be controlled by the control unit, such control unit may control the amount of fluid input, including flow rate or batch quantity. The control unit may also control the heat applied to the inner chamber, including heating times and temperature ranges. The control unit may also control the gas analytical device including carrier gas and entry of components through the device. The control unit may also process the raw data from the gas analytical data and may automatically determine the amounts and types of components in the gas, and in the input fluid as well as the amount of solids, and may display them to a user. The control unit may also control the rotary milling cutter to break up and remove solids, along with any blow-out operation to discharge the solids, and which may be conducted intermittently.

Figure 5:
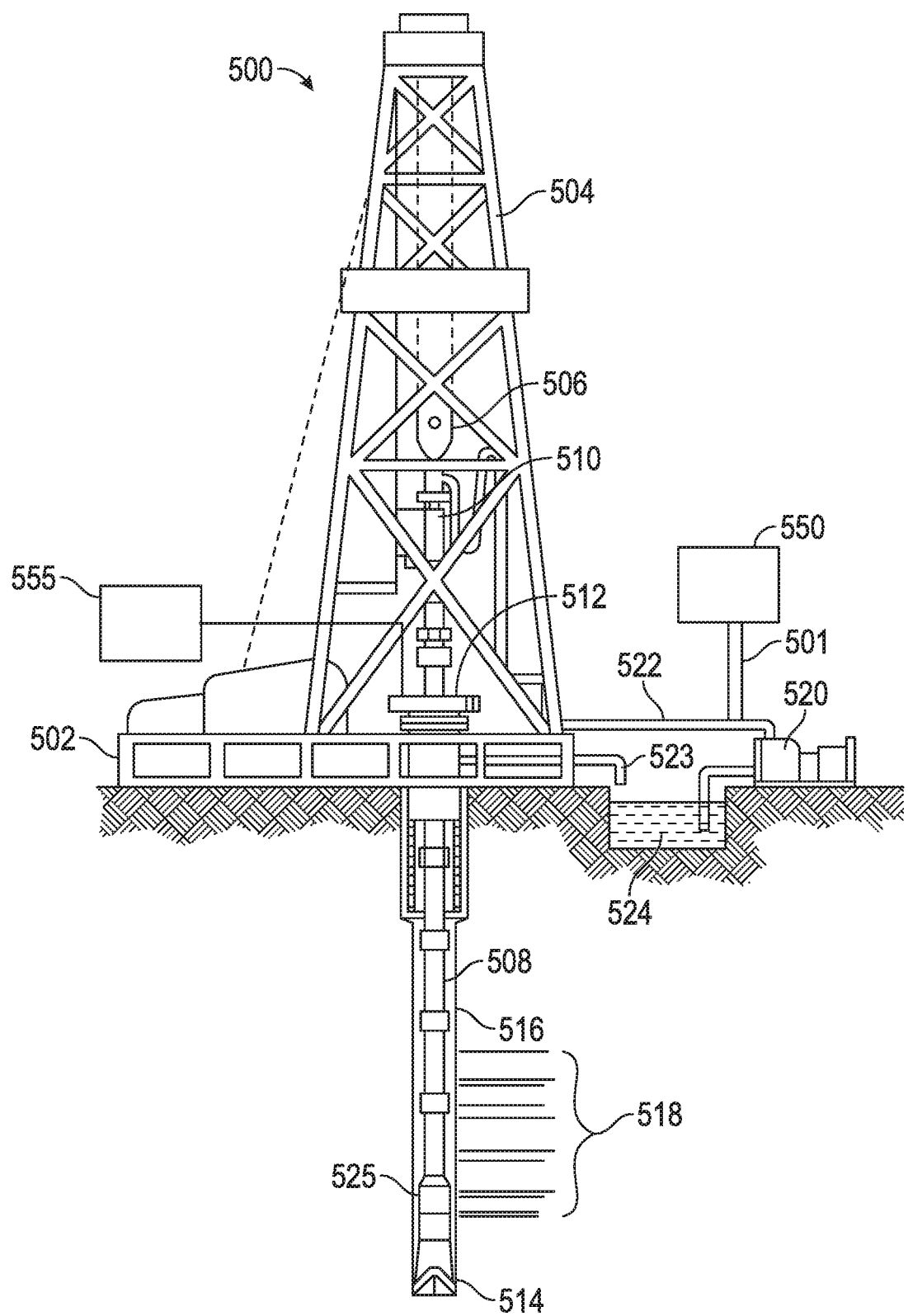
FIG. 5 is a schematic diagram of an example drilling wellbore operating environment, in accordance with some examples.

The disclosure now turns to FIG. 5, which illustrates a schematic view of a drilling wellbore operating environment 500 in accordance with some examples of the present disclosure. As depicted in FIG. 5, a drilling platform 502 can be equipped with a derrick 504 that supports a hoist 506 for raising and lowering a drill string 508. The hoist 506 suspends a top drive 510 suitable for rotating and lowering the drill string 508 through a well head 512. The drill string may contain components for measurement while drilling (MWD) or logging while drilling (LWD) process. A drill bit 514 can be connected to the bottom hole assembly 525 of the drill string 508. As the drill bit 514 rotates, the drill bit 514 creates a wellbore 516 that passes through various formations 518. A pump 520 circulates drilling fluid through a supply pipe 522 to top drive 510, down through the interior of drill string 508 and orifices in drill bit 514, back to the surface via the annulus around drill string 508, and into a retention pit 524. In the illustrated example, the drilling fluid transports cuttings from the wellbore 516 into the retention pit 524 via exit line 523 and aids in maintaining the integrity of the wellbore 516.

A test line can 501 can feed drilling fluid to the fluid composition measurement apparatus 550, which may be the same as the fluid composition measurement apparatus 100 illustrated in FIG. 1. The amounts or fractions of various oil, water, or other volatiles maybe determined as well as the solids amount and fraction, by volume or mass as described hereinabove. The drilling fluid from exit line 523 may also be provided to the fluid composition measurement apparatus 550 for testing as well. A control unit 555 may be communicatively coupled with the drill string to communicate, receive, and/or transmit information via wire or wirelessly with the drill string drill string 508, including control of the drill string or logging operations. The control unit 555 may also may be communicatively coupled with the fluid composition measurement apparatus 550 for evaluating the drilling fluid as described herein, and may/or the fluid composition measurement apparatus 550 includes its own integrated processor.

Figure 6:
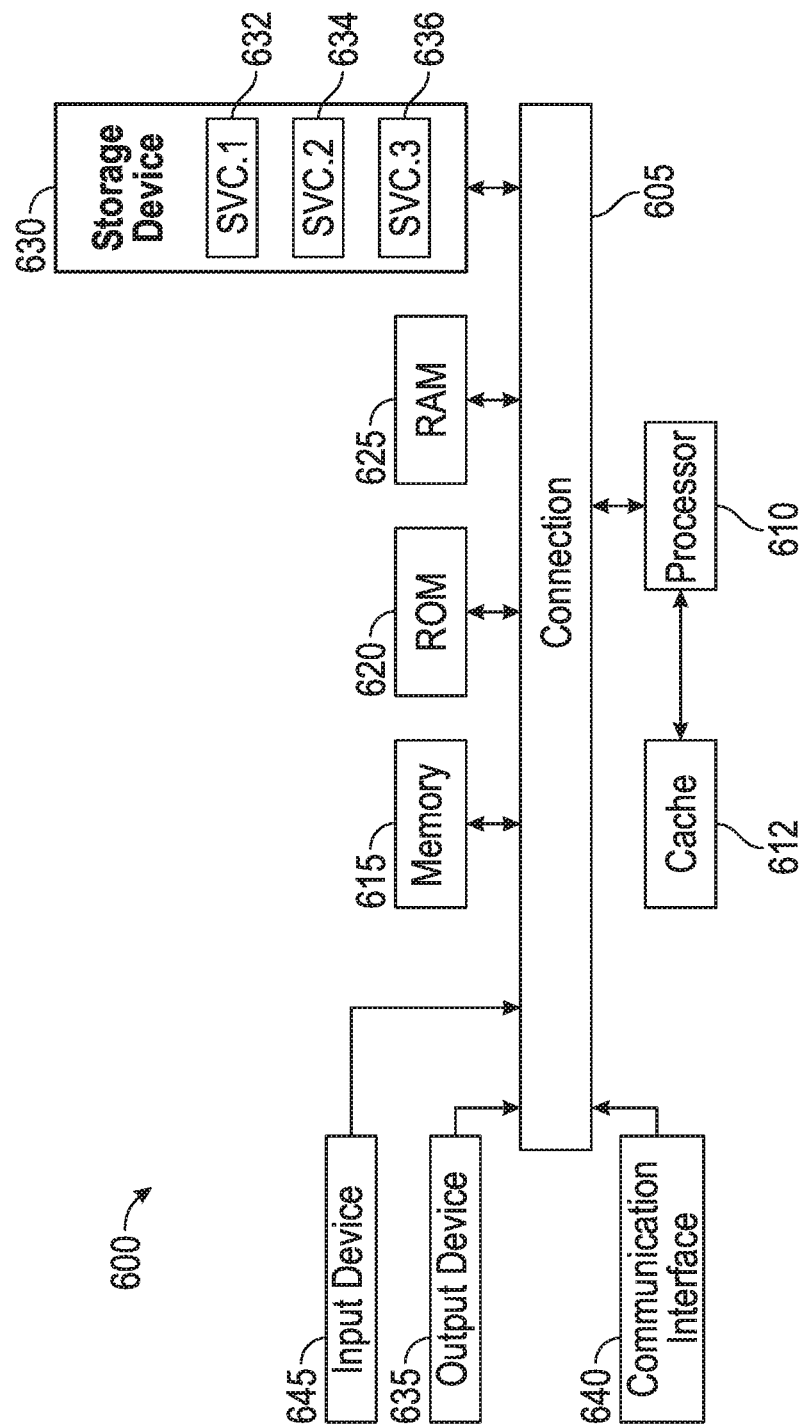
FIG. 6 is a schematic diagram of an example computing device architecture, in accordance with some examples.

Having disclosed example systems, methods, and technologies for determining the relative fraction of components of a fluid, the disclosure now turns to FIG. 6, which illustrates an example computing device architecture 600 which can be employed to perform various steps, methods, and techniques disclosed herein. The various implementations will be apparent to those of ordinary skill in the art when practicing the present technology. Persons of ordinary skill in the art will also readily appreciate that other system implementations or examples are possible.

As noted above, FIG. 6 illustrates an example computing device architecture 600 of a computing device which can implement the various technologies and techniques described herein. For example, the computing device architecture 600 can implement the control unit 147 shown in FIG. 1 and/or the control unit 555 of FIG. 5 and perform various steps, methods, and techniques disclosed herein. The components of the computing device architecture 600 are shown in electrical communication with each other using a connection 605, such as a bus. The example computing device architecture 600 includes a processing unit (CPU or processor) 610 and a computing device connection 605 that couples various computing device components including the computing device memory 615, such as read only memory (ROM) 620 and random access memory (RAM) 625, to the processor 610.

The computing device architecture 600 can include a cache of high-speed memory connected directly with, in close proximity to, or integrated as part of the processor 610. The computing device architecture 600 can copy data from the memory 615 and/or the storage device 630 to the cache 612 for quick access by the processor 610. In this way, the cache can provide a performance boost that avoids processor 610 delays while waiting for data. These and other modules can control or be configured to control the processor 610 to perform various actions. Other computing device memory 615 can be available for use as well. The memory 615 can include multiple different types of memory with different performance characteristics. The processor 610 can include any general purpose processor and a hardware or software service, such as service 1 632, service 2 634, and service 3 636 stored in storage device 630, configured to control the processor 610 as well as a special-purpose processor where software instructions are incorporated into the processor design. The processor 610 can be a self-contained system, containing multiple cores or processors, a bus, memory controller, cache, etc. A multi-core processor can be symmetric or asymmetric.

To enable user interaction with the computing device architecture 600, an input device 645 can represent any number of input mechanisms, such as a microphone for speech, a touch-sensitive screen for gesture or graphical input, keyboard, mouse, motion input, speech and so forth. An output device 635 can also be one or more of a number of output mechanisms known to those of skill in the art, such as a display, projector, television, speaker device, etc. In some instances, multimodal computing devices can enable a user to provide multiple types of input to communicate with the computing device architecture 600. The communications interface 640 can generally govern and manage the user input and computing device output. There is no restriction on operating on any particular hardware arrangement and therefore the basic features here can easily be substituted for improved hardware or firmware arrangements as they are developed.

Storage device 630 is a non-volatile memory and can be a hard disk or other types of computer readable media which can store data that are accessible by a computer, such as magnetic cassettes, flash memory cards, solid state memory devices, digital versatile disks, cartridges, random access memories (RAMs) 625, read only memory (ROM) 620, and hybrids thereof. The storage device 630 can include services 632, 634, 636 for controlling the processor 610. Other hardware or software modules are contemplated. The storage device 630 can be connected to the computing device connection 605. In one aspect, a hardware module that performs a particular function can include the software component stored in a computer-readable medium in connection with the necessary hardware components, such as the processor 610, connection 605, output device 635, and so forth, to carry out the function.

For clarity of explanation, in some instances the present technology can be presented as including individual functional blocks including functional blocks comprising devices, device components, steps or routines in a method embodied in software, or combinations of hardware and software.

In some embodiments the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Methods according to the above-described examples can be implemented using computer-executable instructions that are stored or otherwise available from computer readable media. Such instructions can include, for example, instructions and data which cause or otherwise configure a general purpose computer, special purpose computer, or a processing device to perform a certain function or group of functions. Portions of computer resources used can be accessible over a network. The computer executable instructions can be, for example, binaries, intermediate format instructions such as assembly language, firmware, source code, etc. Examples of computer-readable media that can be used to store instructions, information used, and/or information created during methods according to described examples include magnetic or optical disks, flash memory, USB devices provided with non-volatile memory, networked storage devices, and so on.

Devices implementing methods according to these disclosures can include hardware, firmware and/or software, and can take any of a variety of form factors. Typical examples of such form factors include laptops, smart phones, small form factor personal computers, personal digital assistants, rackmount devices, standalone devices, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are example means for providing the functions described in the disclosure.

In the foregoing description, aspects of the application are described with reference to specific embodiments thereof, but those skilled in the art will recognize that the application is not limited thereto. Thus, while illustrative embodiments of the application have been described in detail herein, it is to be understood that the disclosed concepts can be otherwise variously embodied and employed, and that the appended claims are intended to be construed to include such variations, except as limited by the prior art. Various features and aspects of the above-described subject matter can be used individually or jointly. Further, embodiments can be utilized in any number of environments and applications beyond those described herein without departing from the broader spirit and scope of the specification. The specification and drawings are, accordingly, to be regarded as illustrative rather than restrictive. For the purposes of illustration, methods were described in a particular order. It should be appreciated that in alternate embodiments, the methods can be performed in a different order than that described.

Various materials can be used for drilling fluid, including oil-based fluids and water-based fluids. The drilling fluid can also include additives to improve well performance, control fluid or circulation loss, and/or provide emulsification.

Numerous examples are provided herein to enhance understanding of the present disclosure. A specific set of statements are provided as follows.

Statement 1: An apparatus for measuring a fluid input comprising: a vessel body having an inner chamber coupled with a fluid inlet and an outlet; a heating element coupled with the vessel body operable to communicate heat sufficient to vaporize a fluid within the vessel body to a gas; a gas analytical device coupled with the outlet operable to measure components of the gas exiting the vessel body via the outlet; and a rotary milling cutter translatable through the inner chamber and into solids remaining from the vaporized fluid, and having cutters operable to break the solids within the inner chamber remaining from the vaporized fluid.

Statement 2: The apparatus of Statement 1, further comprising a solids discharge port through which the broken solids exit.

Statement 3: The apparatus of Statement 1 or 2, further comprising a pump for injecting the fluid into the fluid inlet.

Statement 4: The apparatus according to any one of the preceding Statements 1-3, wherein the gas analytical device uses one or more members selected from the group of gas chromatography, mass spectroscopy, spectroscopy, IR spectroscopy, UV-Fluorescence spectroscopy, and UV-VIS spectroscopy.

Statement 5: The apparatus according to any one of the preceding Statements 1-4, wherein the gas analytical device determines chemical components making up the gas.

Statement 6: The apparatus according to any one of the preceding Statements 1-5, wherein the fluid used is drilling fluid comprising at least oil and water.

Statement 7: The apparatus according to any one of the preceding Statements 1-6, wherein the gas analytical device determines the oil and water fraction of gas.

Statement 8: A method comprising: introducing a fluid into an inner chamber of a vessel body; heating the fluid in the vessel body such that the fluid vaporizes to form a gas, whereby solids from the fluid are left within the inner chamber as a result of the vaporization; flowing the gas out the body via an outlet; measuring components of the gas exiting the vessel body with a gas analytical device; milling the solids with a rotary milling cutter; and discharging solids from the inner chamber.

Statement 9: The method of Statement 8, further comprising flushing the inner chamber with an inert gas.

Statement 10: The method of Statement 8 or 9, wherein measuring the components of the gas exiting the body with the gas analytical device comprises determining a hydrocarbon fraction and a water fraction of the gas.

Statement 11: The method according to any one of the preceding Statements 8-10, wherein the gas analytical device to measure components of the gas, uses one or more members selected from the group of gas chromatography, mass spectroscopy, spectroscopy, IR spectroscopy, UV-Fluorescence spectroscopy, and UV-VIS spectroscopy.

Statement 12: The method according to any one of the preceding Statements 8-11, wherein the solids are in the form of a solid puck, and wherein the milling comprises translating cutters within the inner chamber through the solid puck.

Statement 13: The method according to any one of the preceding Statements 8-12, wherein the rotary milling cutter contacts a sidewall of the inner chamber thereby removing solids from the sidewalls during milling.

Statement 14: The method according to any one of the preceding Statements 8-13, wherein the fluid is introduced into the vessel and the gas is measured in a continuous process.

Statement 15: The method according to any one of the preceding Statements 8-14, wherein the fluid introduced into the vessel is introduced at a rate of from about 1 to 10 ml/min.

Statement 16: The method according to any one of the preceding Statements 8-15, wherein the fluid is introduced into the vessel and the gas is measured in a batch process.

Statement 17: The method according to any one of the preceding Statements 8-16, wherein the fluid is drilling fluid from a wellbore.

Statement 18: A system for measuring a fluid input comprising: a vessel body having an inner chamber coupled with a fluid inlet and an outlet; a heating element coupled with the vessel body operable to communicate heat sufficient to vaporize a fluid within the vessel body to a gas; a gas analytical device coupled with the outlet operable to measure components of the gas exiting the vessel body via the outlet; and a rotary milling cutter translatable through the inner chamber and into solids remaining from the vaporized fluid, and having cutters operable to break the solids within the inner chamber remaining from the vaporized fluid.

Statement 19: The system of Statement 18, wherein measuring the components of the gas exiting the body with the gas analytical device comprises determining an oil fraction and a water fraction of the gas.

Statement 20: The system of Statement 18 or 19, wherein the fluid is a drilling fluid received from a wellbore.

What is claimed is:

1. An apparatus for measuring a fluid input comprising: a vessel body having an inner chamber coupled with a fluid inlet and an outlet; a heating element coupled with the vessel body operable to communicate heat sufficient to vaporize a fluid within the vessel body to a gas; a gas analytical device coupled with the outlet operable to measure components of the gas exiting the vessel body via the outlet; and a rotary milling cutter translatable through the inner chamber and into solids remaining from the vaporized fluid, and having cutters operable to break the solids within the inner chamber remaining from the vaporized fluid.

2. The apparatus of claim 1, further comprising a solids discharge port through which the broken solids exit.

3. The apparatus of claim 1, further comprising a pump for injecting the fluid into the fluid inlet.

4. The apparatus of claim 1, wherein the gas analytical device uses one or more members selected from the group of gas chromatography, mass spectroscopy, spectroscopy, IR spectroscopy, UV-Fluorescence spectroscopy, and UV-VIS spectroscopy.

5. The apparatus of claim 1, wherein the gas analytical device determines chemical components making up the gas.

6. The apparatus of claim 1, wherein the fluid used is drilling fluid comprising at least oil and water.

7. The apparatus of claim 6, wherein the gas analytical device determines the oil and water fraction of the gas.

8. A method comprising:
introducing a fluid into an inner chamber of a vessel body;
heating the fluid in the vessel body such that the fluid vaporizes to form a gas, whereby solids from the fluid are left within the inner chamber as a result of the vaporization;
flowing the gas out the body via an outlet;
measuring components of the gas exiting the vessel body with a gas analytical device;
milling the solids with a rotary milling cutter; and
discharging solids from the inner chamber.

9. The method of claim 8, further comprising flushing the inner chamber with an inert gas.

10. The method of claim 8, wherein measuring the components of the gas exiting the body with the gas analytical device comprises determining a hydrocarbon fraction and a water fraction of the gas.

11. The method of claim 8, wherein the gas analytical device to measure components of the gas, uses one or more members selected from the group of gas chromatography, mass spectroscopy, spectroscopy, IR spectroscopy, UV-Fluorescence spectroscopy, and UV-VIS spectroscopy.

12. The method of claim 8, wherein the solids are in the form of a solid puck, and wherein the milling comprises translating cutters within the inner chamber through the solid puck.

13. The method of claim 8, wherein the rotary milling cutter contacts a sidewall of the inner chamber thereby removing solids from the sidewalls during milling.

14. The method of claim 8, wherein the fluid is introduced into the vessel and the gas is measured in a continuous process.

15. The method of claim 14, wherein the fluid introduced into the vessel is introduced at a rate of from about 1 to 10 ml/min.

16. The method of claim 8, wherein the fluid is introduced into the vessel and the gas is measured in a batch process.

17. The method of claim 8, wherein the fluid is drilling fluid from a wellbore.

18. A system for measuring a fluid input comprising: a vessel body having an inner chamber coupled with a fluid inlet and an outlet; a heating element coupled with the vessel body operable to communicate heat sufficient to vaporize a fluid within the vessel body to a gas; a gas analytical device coupled with the outlet operable to measure components of the gas exiting the vessel body via the outlet; and a rotary milling cutter translatable through the inner chamber and into solids remaining from the vaporized fluid, and having cutters operable to break the solids within the inner chamber remaining from the vaporized fluid.

19. The system of claim 18, wherein measuring the components of the gas exiting the body with the gas analytical device comprises determining an oil fraction and a water fraction of the gas.

20. The system of claim 18, wherein the fluid is a drilling fluid received from a wellbore.

* * * * *